(12) United States Patent  
Cullen

(10) Patent No.: US 9,213,022 B1  
(45) Date of Patent: Dec. 15, 2015

(54) LEAD INDICATOR SPRAY

(71) Applicant: John Cullen, Louisville, KY (US)

(72) Inventor: John Cullen, Louisville, KY (US)

( * ) Notice: Subject to any disclaimer, the term of this patent is extended or adjusted under 35 U.S.C. 154(b) by 0 days.

(21) Appl. No.: 14/451,339

(22) Filed: Aug. 4, 2014

Related U.S. Application Data

(60) Provisional application No. 61/862,503, filed on Aug. 5, 2013.

(51) Int. Cl.
*G01N 33/20* (2006.01)
*G01N 21/78* (2006.01)

(52) U.S. Cl.
CPC ............ *G01N 33/20* (2013.01); *G01N 21/78* (2013.01); *Y10T 436/200833* (2015.01); *Y10T 436/203332* (2015.01)

(58) Field of Classification Search
CPC ....... G01N 33/20; G01N 21/77; G01N 21/78; Y10T 436/20; Y10T 436/200833; Y10T 436/203332; Y10T 436/25

USPC ............ 436/73, 77, 127, 128, 131, 164, 166, 436/174; 422/405, 430, 549
See application file for complete search history.

(56) References Cited

U.S. PATENT DOCUMENTS

| | | | | |
|---|---|---|---|---|
| 5,364,792 A | * | 11/1994 | Stone | 436/73 |
| 6,248,593 B1 | * | 6/2001 | Esswein et al. | 436/77 |
| 2006/0160230 A1 | * | 7/2006 | Esswein et al. | 436/77 |
| 2013/0052741 A1 | * | 2/2013 | Gozum | 436/73 |

* cited by examiner

*Primary Examiner* — Maureen Wallenhorst
(74) *Attorney, Agent, or Firm* — Law Office of J L Simunic; Joan L. Simunic

(57) ABSTRACT

The present development is a kit and a method for easily determining the presence of lead on a surface. The kit provides a rhodizonate salt and an aqueous acid mixed together in a container that can deliver a liquid product as a fine particle spray. In a preferred embodiment, the rhodizonate salt is sodium rhodizonate and the aqueous acid is aqueous acetic acid. The method includes mixing sodium rhodizonate and aqueous acetic acid and then delivering it to a surface as a fine particle spray, and monitoring any change of color on the treated surface.

11 Claims, No Drawings

LEAD INDICATOR SPRAY

CROSS-REFERENCE TO PRIOR APPLICATIONS

The present application claims priority to U.S. provisional patent application 61/862,503 filed on Aug. 5, 2013.

BACKGROUND

The present development is a kit to prepare a liquid indicator to detect for the presence of lead on a surface. In a preferred embodiment, the liquid indicator is dispensed from a spray bottle.

Lead is detrimental to the human body and can cause environmental pollution. Thus, there has been an effort to restrict the use of lead-based products, particularly in residential units. However, older dwellings often have residual lead present.

It is often difficult to visually determine whether or not lead is present on a surface. Thus, detection methods have been proposed where easy visual detection of lead is made possible by way of chemical reactions. For example, a lead testing kit based on the lead and rhodizonate ion reaction system is available under the brand "LeadCheck™". In this kit, a solution of sodium rhodizonate and a tartrate buffer is applied to the tip of a swab. The surface to be tested is rubbed with the tip of a swab. If the swab tip changes color to pink or red, the presence of lead is detected; the lack of any color change indicates the absence of significant levels of lead.

SUMMARY OF THE PRESENT INVENTION

The present development is a kit comprising a spray top container containing a predetermined quantity of dry rhodizonate salt and an aqueous acid having a pH between 2.0 and 3.0. The rhodizonate salt and the acid are combined in the spray top container and sprayed on a surface. A visible color change to pink or red indicates the presence of lead on the surface. In a preferred embodiment the rhodizonate salt is sodium rhodizonate and the acid is aqueous acetic acid.

DETAILED DESCRIPTION OF THE INVENTION

The following description is intended to provide the reader with a better understanding of the invention. The description is not intended to be limiting with respect to any element not otherwise limited within the claims.

The present development is a kit and a method for easily determining the presence of lead on a surface. The kit comprises a rhodizonate salt and an aqueous acid having a pH of 2.0 to 3.0, wherein the salt and acid are mixed together in a container suitable for delivering a liquid product as a fine particle spray. The method comprises mixing a rhodizonate salt and an aqueous acid and then delivering it to a surface using a container suitable for delivering a liquid product as a fine particle spray, and monitoring any change of color on the treated surface.

The rhodizonate salt may be any rhodizonate salt that will easily release a rhodizonate anion, $C_6O_6^=$. Exemplary counter-ions are sodium, potassium, cesium and rubinium. Exemplary rhodizonate salts are sodium rhodizonate, potassium rhodizonate, and combinations thereof. In a preferred embodiment, the rhodizonate salt is sodium rhodizonate.

The aqueous acid may be any essentially colorless acid having a pH of from about 2.0 to about 3.0. Exemplary acids include, without limitation, aqueous acetic acid, common table vinegar, aqueous citric acid, and combinations thereof.

In a preferred embodiment, the aqueous acid is aqueous acetic acid, preferably being up to 10 wt % acetic acid, more preferably being from about 3 wt % to about 7 wt % acetic acid.

In a first embodiment, a container suitable for delivering a liquid product as a fine particle spray is provided. An exemplary container is one having a pump delivery system similar to that used for non-aerosolized hair spray. The aqueous acid is provided in the spray container. The rhodizonate salt is provided in a powdered form, preferably delivered in a small disposable package. An exemplary packing material is a foil-lined pouch with crimped ends, at least one of which can easily be torn open, similar to the pouches used to deliver powdered flavorings for individual water bottles.

Shortly before use, a user combines the rhodizonate salt with the aqueous acid in the spray bottle, mixes until the rhodizonate salt dissolves, and then sprays the resulting mixture onto the lead-suspected surface. If the salt-acid mixture displays a color change from essentially colorless to pink or red, the surface most likely contains measureable quantities of lead. If no color change occurs, there is essentially no available lead present, such as lead paint dust. The solution normally remains active for lead detection for about 60 minutes after the rhodizonate salt is combined with the aqueous acid.

In a first alternative embodiment, the rhodizonate salt is provided in the spray container and the aqueous acid is provided in a separate container. Any container suitable for supplying a mild acid solution may be used.

It is understood that one skilled in the art may make alterations to the embodiments shown and described herein without departing from the scope of the invention.

What is claimed is:

1. A kit for detecting lead present on a surface, the kit consisting essentially of:
   a) a container configured for delivering a liquid product as a fine particle spray;
   b) an aqueous acid having a pH between 2.0 and 3.0, said acid provided in a first package; and,
   c) a rhodizonate salt in a powdered form, said salt provided in a second package.

2. The kit of claim 1 wherein said first package is said spray container.

3. The kit of claim 1 wherein said second package is said spray container.

4. The kit of claim 1 wherein said second package is a foil-lined pouch.

5. The kit of claim 1 wherein said container configured for delivering a liquid product includes a pump aerosol spritzer.

6. The kit of claim 1 wherein said aqueous acid is selected from the group consisting of aqueous acetic acid, aqueous citric acid, and combinations thereof, and wherein said rhodizonate salt is selected from the group consisting of sodium rhodizonate, potassium rhodizonate, and combinations thereof.

7. The kit of claim 6 wherein said aqueous acid comprises up to about 10 wt % acetic acid.

8. A method of detecting lead on a surface, the method comprising:
   a) providing a container configured for delivering a liquid product as a fine particle spray;
   b) providing an aqueous acid having a pH of from 2.0-3.0;
   c) providing a rhodizonate salt in a powdered form;
   d) combining said rhodizonate salt with said aqueous acid in said spray container;
   e) agitating said container until said rhodizonate salt is essentially dissolved to produce a rhodizonate salt—aqueous acid solution; and, f) applying said rhodizonate salt—aqueous acid solution to a surface as a fine particle spray; and, g) determining if a color change indicating the presence of lead has occurred.

9. The method of claim 8 wherein said aqueous acid is selected from the group consisting of aqueous acetic acid, aqueous citric acid, and combinations thereof.

10. The method of claim 8 wherein said rhodizonate salt is selected from the group consisting of sodium rhodizonate, potassium rhodizonate, and combinations thereof.

11. The method of claim 8 wherein said container configured for delivering a liquid product includes a pump aerosol spritzer.

\* \* \* \* \*